US012697401B2

(12) United States Patent
Sullenger et al.

(10) Patent No.: US 12,697,401 B2
(45) Date of Patent: Aug. 4, 2026

(54) THROMBUS IMAGING APTAMERS AND METHODS OF USING SAME

(71) Applicant: Duke University, Durham, NC (US)

(72) Inventors: Bruce A. Sullenger, Durham, NC (US); Kady-Ann C. Steen-Burrell, Durham, NC (US); Bethany Powell Gray, Durham, NC (US)

(73) Assignee: Duke University, Durham, NC (US)

( * ) Notice: Subject to any disclaimer, the term of this patent is extended or adjusted under 35 U.S.C. 154(b) by 518 days.

(21) Appl. No.: 18/086,378

(22) Filed: Dec. 21, 2022

(65) Prior Publication Data

US 2023/0330271 A1 Oct. 19, 2023

Related U.S. Application Data

(62) Division of application No. 16/880,791, filed on May 21, 2020, now Pat. No. 11,565,002, which is a division of application No. 15/570,065, filed as application No. PCT/US2016/029745 on Apr. 28, 2016, now Pat. No. 10,660,973.

(60) Provisional application No. 62/157,725, filed on May 6, 2015, provisional application No. 62/153,870, filed on Apr. 28, 2015.

(51) Int. Cl.
| | |
|---|---|
| *A61K 49/00* | (2006.01) |
| *C07H 21/02* | (2006.01) |
| *C12N 15/115* | (2010.01) |

(52) U.S. Cl.
CPC ...... *A61K 49/0002* (2013.01); *A61K 49/0021* (2013.01); *A61K 49/0032* (2013.01); *A61K 49/0054* (2013.01); *C07H 21/02* (2013.01); *C12N 15/115* (2013.01); *C12N 2310/113* (2013.01); *C12N 2310/16* (2013.01); *C12N 2310/317* (2013.01); *C12N 2310/3517* (2013.01)

(58) Field of Classification Search
CPC ............... A61K 49/00; A61K 49/0002; A61K 49/0021; A61K 49/0032; A61K 49/0054; C07H 21/02; C12N 15/115; C12N 2310/113; C12N 2310/16; C12N 2310/317; C12N 2310/3517; C12N 2310/321; C12N 2310/3521; C12N 2310/322; C12N 2310/3533
See application file for complete search history.

(56) References Cited

U.S. PATENT DOCUMENTS

| | | | |
|---|---|---|---|
| 5,660,985 | A | 8/1997 | Pieken et al. |
| 5,756,291 | A | 5/1998 | Griffin et al. |
| 5,770,198 | A | 6/1998 | Coller et al. |
| 6,376,190 | B1 | 4/2002 | Gold et al. |
| 6,780,850 | B1 | 8/2004 | Dougan |
| 6,855,496 | B2 | 2/2005 | Pagratis et al. |
| 7,300,922 | B2 | 11/2007 | Sullenger et al. |
| 7,304,041 | B2 | 12/2007 | Rusconi |
| 7,312,325 | B2 | 12/2007 | Sullenger et al. |
| 7,566,701 | B2 | 7/2009 | Diener et al. |
| 7,741,307 | B2 | 6/2010 | Sullenger et al. |
| 7,776,836 | B2 | 8/2010 | Sullenger et al. |
| 8,367,627 | B2 | 2/2013 | Sullenger |
| 8,790,924 | B2 | 7/2014 | Sullenger |
| 9,061,043 | B2 | 6/2015 | Sullenger |
| 9,150,867 | B2 | 10/2015 | Maher, III et al. |
| 9,687,529 | B2 | 6/2017 | Sullenger |
| 9,873,727 | B2 | 1/2018 | Sullenger |
| 9,958,448 | B2 | 5/2018 | Halbert et al. |
| 10,350,158 | B2 | 7/2019 | Lee et al. |
| 10,533,059 | B2 | 1/2020 | Sengupta et al. |
| 10,660,973 | B2 * | 5/2020 | Sullenger .......... A61K 49/0002 |
| 11,421,234 | B2 | 8/2022 | Ma et al. |
| 11,565,002 | B2 * | 1/2023 | Sullenger .......... A61K 49/0021 |
| 2003/0083294 | A1 | 5/2003 | Sullenger |
| 2003/0143217 | A1 | 7/2003 | Baird et al. |
| 2003/0153506 | A1 | 8/2003 | Bylund et al. |
| 2003/0158120 | A1 | 8/2003 | Mattsson |
| 2003/0175703 | A1 | 9/2003 | Sullenger et al. |
| 2005/0176940 | A1 | 8/2005 | King |
| 2006/0193821 | A1 | 8/2006 | Diener et al. |
| 2006/0264369 | A1 | 11/2006 | Diener et al. |
| 2008/0051339 | A1 | 2/2008 | Sullenger et al. |

(Continued)

FOREIGN PATENT DOCUMENTS

| | | |
|---|---|---|
| WO | 2002/026932 | 4/2002 |
| WO | 2006/033854 | 3/2006 |

(Continued)

OTHER PUBLICATIONS

Yamaguchi et al., "Studies of a microchip flow-chamber system to characterize whole blood thrombogenicity in healthy individuals," (2013) Thrombosis research 132:263-70.

(Continued)

*Primary Examiner* — D. L. Jones

(74) *Attorney, Agent, or Firm* — Quarles & Brady, LLP

(57) ABSTRACT

Provided herein are imaging agents, antidotes to the imaging agents and methods of using the same to image a thrombus or blood clot or thrombin including sites of thrombin accumulation and to diagnose and treat thrombosis. The imaging agents include an aptamer capable of binding the thrombus or thrombin in particular linked to a reporter moiety. The imaging agents may be used to label the thrombus or sites of thrombin accumulation. Antidotes capable of binding to the aptamer in the imaging agent are also provided. The antidotes may further be linked to a quencher capable of quenching the reporter moiety.

17 Claims, 10 Drawing Sheets

Specification includes a Sequence Listing.

(56) References Cited

U.S. PATENT DOCUMENTS

| 2008/0207546 A1 | 8/2008 | Sullenger |
| 2008/0220055 A1 | 9/2008 | Ludwig et al. |
| 2009/0048193 A1 | 2/2009 | Rusconi et al. |
| 2010/0003244 A1 | 1/2010 | Munch et al. |
| 2010/0076060 A1 | 3/2010 | Sullenger et al. |
| 2010/0184822 A1 | 7/2010 | Sullenger et al. |
| 2010/0249217 A1 | 9/2010 | Sullenger et al. |
| 2010/0297654 A1 | 11/2010 | Heyduk |
| 2010/0311820 A1 | 12/2010 | Layzer et al. |
| 2010/0324120 A1 | 12/2010 | Chen et al. |
| 2011/0118187 A1 | 5/2011 | Sullenger et al. |
| 2011/0160443 A1 | 6/2011 | Sullenger et al. |
| 2012/0264815 A1 | 10/2012 | Sullenger et al. |
| 2014/0050717 A1 | 2/2014 | Dockal et al. |
| 2014/0348755 A1 | 11/2014 | Weng |
| 2015/0307883 A1 | 10/2015 | Yarden |
| 2016/0130585 A1 | 5/2016 | Casella et al. |
| 2018/0117182 A1 | 5/2018 | Sullenger et al. |
| 2020/0095636 A1 | 3/2020 | Sullenger |
| 2020/0353102 A1 | 11/2020 | Sullenger et al. |

FOREIGN PATENT DOCUMENTS

| WO | 2006/067173 | 6/2006 |
| WO | 2007/035532 | 3/2007 |
| WO | 2018/053427 | 3/2018 |
| WO | 2018/175918 | 9/2018 |
| WO | 2020/086996 | 4/2020 |

OTHER PUBLICATIONS

Bompiani et al., "Probing the Coagulation Pathway with Aptamers Identifies Combinations that Synergistically Inhibit Blood Clot Formation" (2014) Chemistry & Biology 21: 935-944.

Dougan et al., "Evaluation of DNA aptamers directed to thrombin as potential thrombus imaging agents," (2003) Nuclear Medicine and Biology 30:61-72.

Edmunds & Coleman, "Thrombin During Cardiopulmonary Bypass," (2006) The Annals of Thoracic Surgery 82:2315-22.

Franciscis et al., "Nucleic Acid Aptamers for In Vivo Molecular Imaging," (2012) Molecular Imaging Chapter 5.

Giardino et al., "Cooperative antithrombotic effect from the simultaneous inhibition of thrombin and factor Xa," (2010) Blood Coagulation & Fibrinolysis 21: 128-134.

Gunaratne, R. et al. "Combination of aptamer and drug for reversible anticoagulation in cardiopulmonary bypass" Nat Biotechnol. Aug. 2018;36(7):606-613. doi: 10.1038/nbt.4153. Epub Jun. 4, 2018.

Hemker et al., "Calibrated automated thrombin generation measurement in clotting plasma," (2003) Pathophysiol Haemost Thromb 33: 4-15.

Hoffman et al., "A cell-based model of hemostasis," (2001) Thrombosis and haemostasis 85:958-65.

International Search Report and Written Opinion for PCT/US2006/036109 dated Sep. 5, 2007.

International Search Report and Written Opinion for PCT/US2007/022358 dated Aug. 18, 2008.

International Search Report and Written Opinion for PCT/US2008/004119 dated Jun. 26, 2008.

International Search Report and Written Opinion for PCT/US2012/036783 dated Nov. 23, 2012.

International Search Report and Written Opinion for PCT/US2016/029745 dated Oct. 7, 2016.

James et al., "A molecular imaging primer: modalities, imaging agents, and applications," (2012) Physiol Rev 92(2):897-965.

Joachimi, A. et al., "A new anticoagulant-antidote pair: Control of thrombin activity by aptamers and porphyrins," (2007) Journal of the American Chemical Society 129(11):3036-3037.

Keefe, A.D. et al. (2010). Aptamers as therapeutics. Nature reviews Drug discovery, 9(7), 537-550.

Kiefer, T.L. et al., "Inhibitors of platelet adhesion," (2009) Circulation 120:2488-2495.

Koster et al., ""High antithrombin III levels attenuate hemostatic activation and leukocyte activation during cardiopulmonary bypass,"" (2003) Journal of Thoracic &Cardiovascular Surgery 126: 906-7.

Li, M. et al., "Selecting aptamers for a glycoprotein through the incorporation of the boronic acid moiety," (2008) J. Am. Chem. Soc. 130(38):12636-12638.

Long, S.B., et al., "Crystal Structure of an RNA aptamer bound to thrombin," (2008) RNA 14:2504-2512.

Mackman, N., "Triggers, targets and treatments for thrombosis," (2008) Nature 451(7181):914-918.

Maier, K. E., et al. (2016). A new transferrin receptor aptamer inhibits new world hemorrhagic fever mammarenavirus entry. Molecular Therapy-Nucleic Acids, 5, e321.

Monroe et al., "Platelets and thrombin generation," (2002) Arterioscler Thromb Vasc Biol 22:138 1-9.

Musumeci, D. & Montesarchio, D. "Polyvalent nucleic acid aptamers and modulation of their activity: a focus on the thrombin binding aptamer" Pharmacol Ther. Nov. 2012;136(2):202-15. doi: 10.1016/j.pharmthera.2012.07.011. Epub Jul. 28, 2012.

Nimjee et al., "Aptamers as Therapeutics," (2017) Annual review of pharmacology and toxicology 57:61-79.

Nimjee et al., "Synergistic effect of aptamers that inhibit exosites 1 and 2 on thrombin," (2009) RNA 15:2105-11.

Office Action for U.S. Appl. No. 11/992,125 mailed Apr. 9, 2012.

Office Action for U.S. Appl. No. 11/992,125 mailed Aug. 16, 2011.

Office Action for U.S. Appl. No. 13/296,045 mailed Aug. 6, 2012.

Office Action for U.S. Appl. No. 13/878,539 mailed Dec. 8, 2014.

Office Action for U.S. Appl. No. 13/878,539 mailed Jul. 22, 2014.

Office Action for U.S. Appl. No. 12/311,943 mailed Jun. 21, 2013.

Office Action for U.S. Appl. No. 12/311,943 mailed May 10, 2012.

Office Action for U.S. Appl. No. 13/296,045 mailed dated Oct. 22, 2013.

Office Action for U.S. Appl. No. 14/115,797 mailed Sep. 17, 2015.

Oney, et al., "Antidote-controlled platelet inhibition targeting von Willebrand factor with aptamers," (2007) Oligonucleotides 17(3):265-274—Abstract.

Oney, S. et al., "Development of universal antidotes to control aptamer activity," (2009) Nature Medicine, 15(10):1224-1229.

Que-Gewirth, N.S. et al., "Gene therapy progress and prospects: RNA aptamers," (2007) Gene Therapy 14(4):283-291.

Quinn et al., "A guide for diagnosis of patients with arterial and venous thrombosis," (2000) J. Clin. Lab. Sci. 13(4):229-238.

Reikvam et al., "Thrombelastography," (2009) Transfus Apher Sci; 40: 119-23.

Restriction Requirement dated Jan. 8, 2019 for U.S. Appl. No. 15/570,065.

Rusconi, C.P. et al., "Antidote-mediated control of an anticoagulant aptamer in vivo," (2004) Nature Biotechnology 22(11):1423-1428.

Soule, E.E. et al. "Targeting Two Coagulation Cascade Proteases with a Bivalent Aptamer Yields a Potent and Antidote-Controllable Anticoagulant" Nucleic Acid Ther. Feb. 1, 2016; 26(1): 1-9.

Steen-Burrell et al., "Development of an Antidote-Controlled RNA Probe for Molecular Thrombi Imaging," Abstract submitted to Arteriosclerosis, Thrombosis and Vascular Biology (ATVB) Meeting. May 2015.

Wang et al., "A DNA aptamer which binds to and inhibits thrombin exhibits a new structural motif for DNA," (1993) Biochemistry 32:1899-1904.

Wang et al., "Aptamers as therapeutics in cardiovascular diseases," (2011) Curr Med Chem 18:4169-74.

Werstrick et al., "Murine Models of Vascular Thrombosis," (2007) Arterioscler Thromb Vasc Biol 27:2079-2093.

White, R et al., "Generation of Species Cross-reactive Aptamers Using Toggle SELEX," (2001) Molecular Therapy 4(6):567-573.

Wolberg, "Thrombin generation and fibrin clot structure," (2007) Blood Rev 21: 131-42.

Woodruff, R.S. & Sullenger, B.A. "Modulation of the Coagulation Cascade Using Aptamers" Arteriosclerosis, Thrombosis, and Vascular Biology, 35(10):2083-2091 (2015).

* cited by examiner

Tog25t (SEQ ID NO: 1)

Tog25t Control 1 (SEQ ID NO: 5)
and Control 2 (SEQ ID NO: 6)

Control1

Control2

Tog25t Control 3 (SEQ ID NO: 7)

FIGURE 4
FIGURE 4A
| AO4 – GGG UAA GUA CUU CAG (SEQ ID NO: 2) |
| AO5 – UUC AGC UUU GUU CCC (SEQ ID NO: 3) |
| AO6 – UAA GUA CUU CAG CUU U (SEQ ID NO: 4) |
FIGURE 4B
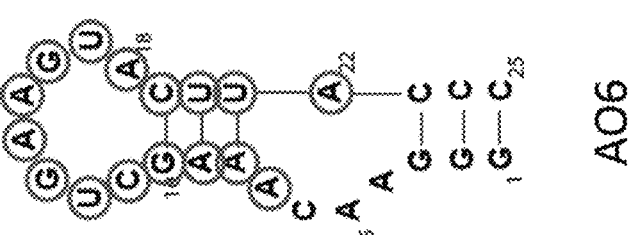
AO6
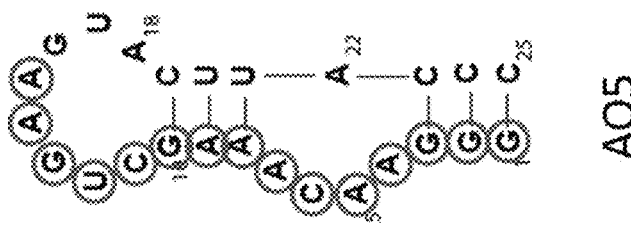
AO5
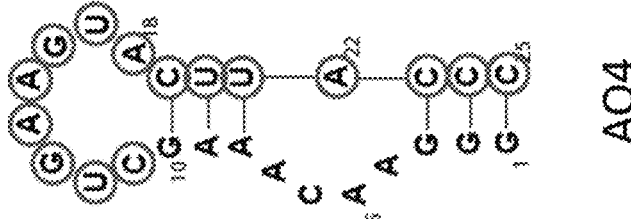
AO4

FIGURE 7

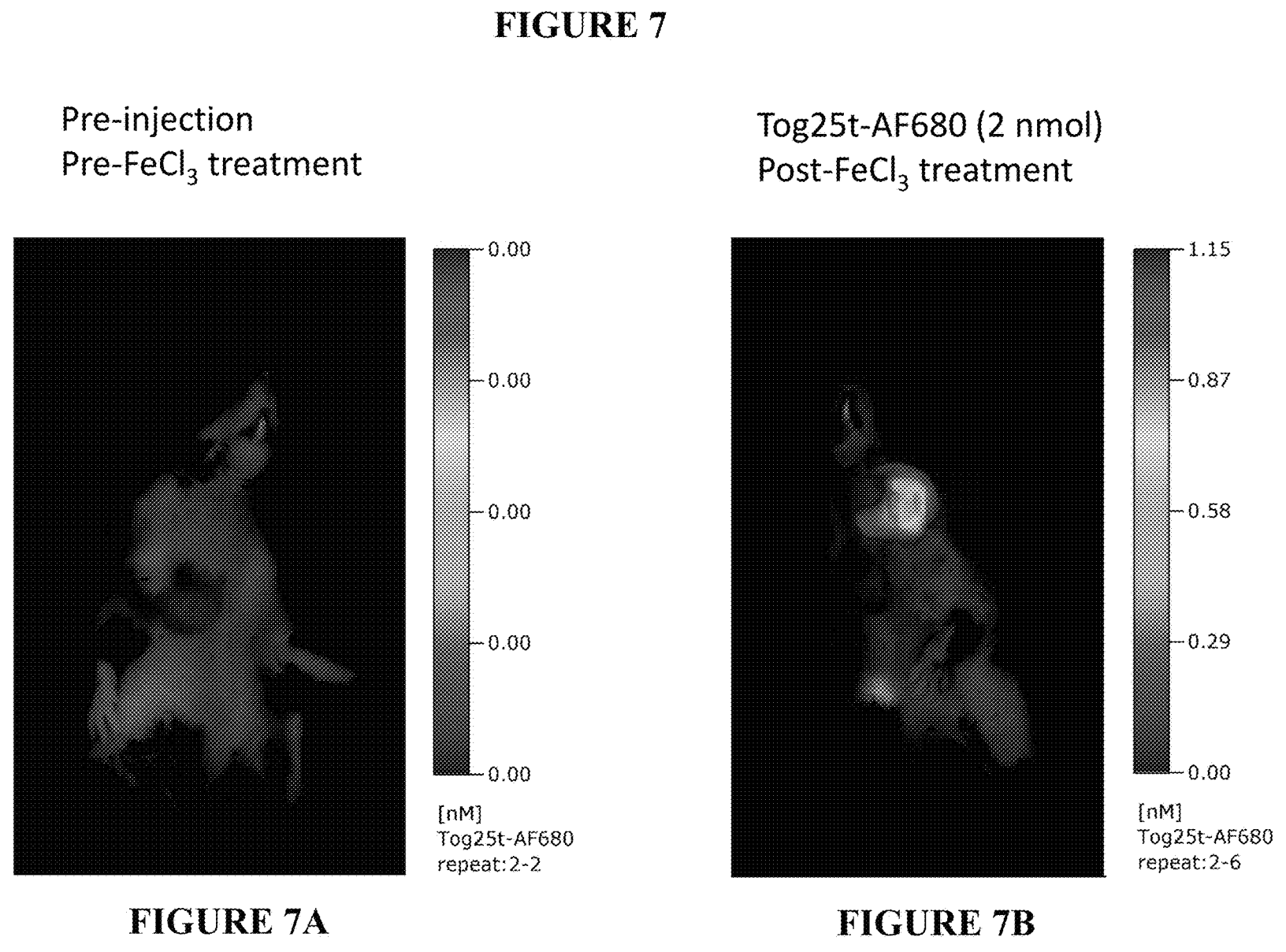

Pre-injection
Pre-FeCl₃ treatment

[nM]
Tog25t-AF680
repeat:2-2

FIGURE 7A

Tog25t-AF680 (2 nmol)
Post-FeCl₃ treatment

[nM]
Tog25t-AF680
repeat:2-6

FIGURE 7B

Control2-AF680 (2 nmol)
Post-FeCl$_3$ treatment

[nM]
Control2-AF68-
0:1-4

Saline
Post-FeCl$_3$ treatment

[nM]
Tog25t-AF680
repeat:1-1

FIGURE 9
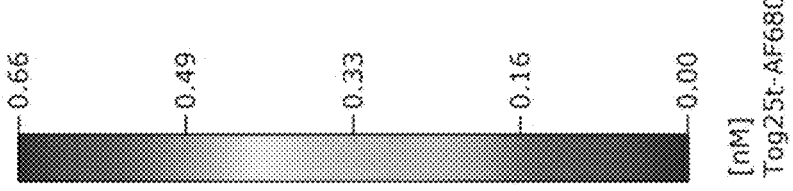
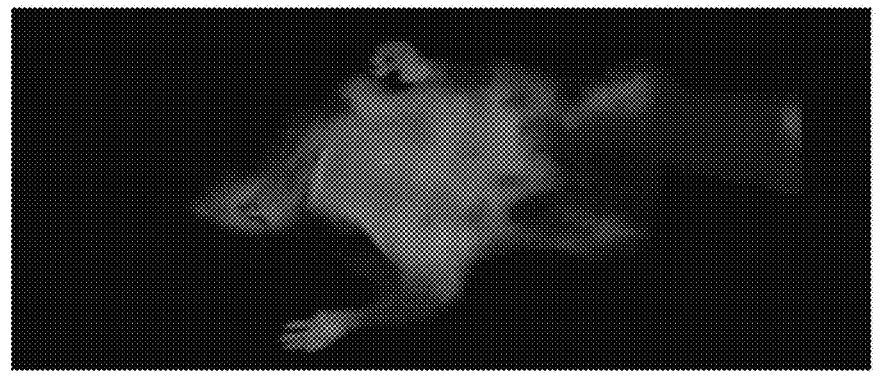
Pre-injection
Pre-FeCl$_3$ treatment
FIG. 9A
Tog25t-AF680 (2nmol)
Post-FeCl$_3$ treatment
FIG. 9B
Tog25t-AF680 (2nmol)
Post-FeCl$_3$ treatment
+ AO4 (5-fold excess)
FIG. 9C
0.66
0.49
0.33
0.16
0.00
[nM]
Tog25t-AF680

Splenic Panc02 Tumors

FIG. 10B

Pancreatic Panc02 Tumors

THROMBUS IMAGING APTAMERS AND METHODS OF USING SAME

CROSS-REFERENCE TO RELATED PATENT APPLICATIONS

The present application is a divisional application of U.S. patent application Ser. No. 16/880,791, filed May 21, 2020, and issued as U.S. Pat. No. 11,565,002, on Jan. 31, 2023, which is a divisional application of U.S. patent application Ser. No. 15/570,065, filed Oct. 27, 2017, and issued as U.S. Pat. No. 10,660,973, on May 26, 2020, which is a national stage filing under 35 U.S.C. § 371 of International Application No. PCT/US2016/029745, filed Apr. 28, 2016, which claims the benefit of priority to U.S. Provisional Application No. 62/153,870, filed on Apr. 28, 2015, and U.S. Provisional Patent Application No. 62/157,725, filed on May 6, 2015, the contents of all of which are incorporated herein by reference in their entirety.

STATEMENT REGARDING FEDERALLY SPONSORED RESEARCH

This invention was made with government support by the National Institutes of Health under Award Number U54HL112307. The government has certain rights in the invention.

SEQUENCE LISTING

This application is being filed electronically via Patent Center and includes an electronically submitted Sequence Listing in xml format. The xml file contains a sequence listing entitled "155554.00541_Sequence Listing.xml" created on May 10, 2023 and is 13,598 bytes in size. The Sequence Listing contained in this.xml file is part of the specification and is hereby incorporated by reference herein in its entirety.

INTRODUCTION

Vascular thrombosis is a major underlying factor in many cardiovascular diseases and is also a major post-surgical complication. Early detection and treatment of thrombi improves outcomes for patients since the responsiveness of thrombi to fibrinolytic treatment decreases with thrombus age. The serine protease, thrombin, plays a central role in thrombogenesis and remains associated with the thrombus thereby facilitating further activation of coagulation factors and platelets after initial clot formation.

Aptamers are single-stranded oligonucleotide ligands that bind specifically to their targets with high affinity. Aptamers can be generated against target molecules, such as soluble coagulation proteins, by screening combinatorial oligonucleotide libraries for high affinity binding to the target (Ellington and Szostak, *Nature* 1990; 346:8 18-22 (1990), Tuerk and Gold, Science 249:505-1 0 (1990)). This selection method has been employed to generate modified RNA aptamers that bind specifically to several coagulation proteins including coagulation factor VIIa (FVIIa) (Layzer and Sullenger, *Oligonucleotides* 17:1-11 (2007)), factor IXa (FIXa) (Rusconi et al, *Nature* 419:90-4 (2002)), factor X (FXa) (Buddai et al, *J Bio Chem* 285:52 12-23 (2010)), and prothrombin/thrombin (Layzer and Sullenger, *Oligonucleotides* 17:1-11 (2007), Bompiani et al, *J Thromb Haemost* 10:870-80 (2012)). Several aptamers bind to both the zymogen and enzyme forms of the protein, and mechanistic studies with the FIXa, FXa, and prothrombin/thrombin aptamers indicate that the aptamers bind a large surface area on the zymogen/enzyme that is critical for procoagulant protein-protein interactions (Buddai et al, *J Bio Chem* 285: 52 12-23 (2010), Bompiani et al, *J Thromb Haemost* 10:870-80 (2012), Long et al, *RNA* 14:1-9 (2008), Sullenger et al, *J Biol Chem* 287:12779-86 2012)). Moreover, two independent types of antidotes have been developed that can rapidly modulate aptamer function, which allows rapid reversal or neutralization of aptamer function (Rusconi et al, *Nature* 419:90-4 (2002), Oney et al, *Nat Med* 15:1224-8 (2009)).

SUMMARY

The present invention results from studies using aptamers to image thrombi and thrombin and addresses the need in the art for new reversible imaging agents and methods for imaging thrombi and thrombin. The results demonstrate that aptamer-based imaging agents are useful tools for detecting thrombi and activated thrombin and may be used to elucidate the complex role proteins, such as thrombin, play in thrombi formation and blood biology. Provided herein are imaging agents and antidotes as well as methods for imaging thrombi and thrombin and for generating subtraction images using aptamer-based imaging agents and antidotes.

In one aspect, imaging agents are provided which comprise (a) an aptamer linked to (b) a reporter moiety. The aptamer is capable of binding thrombin with a Kd<1 µM, 500 nM, 250 nM, 100 nM, 50 nM, 10 nM, 1 nM, 0.5 nM or 0.1 nM. The aptamer may comprise a nucleotide sequence having at least 50%, 60%, 70%, 80%, 90% or 95% sequence identity to GGGAACAAAGCUGAAGUACUUACCC (Tog25t; SEQ ID NO: 1). Alternatively, the aptamer may comprise a nucleotide sequence including from 5' to 3' a first stem forming region comprising at least three nucleotides, a first loop region comprising the nucleotide sequence AACA (adenine-adenine-cytosine-adenine), a second stem forming region comprising at least three nucleotides, a second loop region comprising the nucleotide sequence C U/A GXAG U/A A, a third stem forming region comprising at least three nucleotides capable of forming a stem with the second stem forming region, a third loop region comprising at least one nucleotide and up to 5 nucleotides, and a fourth stem forming region comprising at least three nucleotides capable of forming a stem with the first stem forming region. The single letter codes stand for the traditional bases found in DNA or RNA and the X indicates that any of the four bases may be present at that position. In one embodiment of the aptamer, the nucleotide in the third loop region may be an adenine (A).

In another aspect, antidotes to the aptamers in the imaging agents are provided and may comprise a nucleotide sequence having at least 50%, 60%, 70%, 80%, 90% or 95% sequence identity to one of the following sequences: GGGUAAGUACUUCAG (AO4; SEQ ID NO: 2), UUCAGCUUUGUUCCC (AO5; SEQ ID NO: 3) or UAAGUACUUCAGCUUU (AO5: SEQ ID NO: 4). Additionally, the antidotes may comprise a nucleotide sequence having 50%, 60%, 70%, 80%, 90%, 95%, or 100% sequence identity to a sequence complementary to and/or capable of hybridizing to at least 5, 6, 7, 8, 9, 10, 11, 12, 13, 14, 15, 16, 17, 18, 19, or 20 nucleotides present in the aptamers disclosed herein. The antidotes can be RNA, DNA or comprise modified bases. If DNA, the uracils in SEQ ID NOs: 2-4 are thymines instead.

In another aspect, methods for imaging thrombi are provided. Such methods comprise administering an imaging agent to a subject or contacting a thrombus with the imaging agent, and generating an image of at least a portion of the subject or the thrombus using an imaging modality. The imaging agent comprises an aptamer and a reporter moiety and is capable of specifically labeling the thrombi in the image by binding of the aptamer to the thrombi.

In another aspect, methods for imaging thrombin are provided. Such methods comprise administering an imaging agent to a subject or contacting thrombin with the imaging agent, and generating an image of at least a portion of the subject or the thrombin using an imaging modality. The imaging agent comprises an aptamer and a reporter moiety and is capable of specifically labeling the thrombin in the image by binding of the aptamer to the thrombin.

In a further aspect, methods for generating a subtraction image are provided. The methods include administering an imaging agent to a subject or contacting a thrombus or thrombin with the imaging agent, generating a first image of the subject or thrombus or thrombin, administering an antidote to the subject or contacting the thrombus or thrombin with the antidote, generating a second image of the subject or the thrombus or thrombin, and subtracting the second image from said first image to generate said subtraction image. The imaging agent comprises an aptamer and a reporter moiety. The antidote is capable of binding the aptamer.

BRIEF DESCRIPTION OF THE DRAWINGS

FIG. 4 shows the sequence and base pairing sites of antidote oligonucleotides to Tog25t (AO4 (SEQ ID NO: 2), AO5 (SEQ ID NO: 3), and AO6 (SEQ ID NO: 4)). FIG. 4A shows the nucleotide sequence of the AO4-6 antidotes listed 5' to 3'. FIG. 4B shows the binding sites on Tog25t for each antidote (AO4-6).

FIG. 7 shows near-infrared fluorescence images showing Tog25t-AF680 binding to a $FeCl_3$-induced jugular vein thrombus in vivo in a mouse. The image to the left (FIG. 7A)

shows a mouse before treatment with ferric chloride ($FeCl_3$) to induce a thrombus and before injection of the Tog25t-AF680 aptamer. The image to the right (FIG. 7B) shows localization of fluorescence close to the site of injury (thrombus) following treatment with ferric chloride ($FeCl_3$) and following injection of the Tog25t-AF680 aptamer.

Figures 8, 8A, 8B:

FIG. 8 shows near-infrared fluorescence images of mice after jugular vein thrombi formation using $FeCl_3$. The image to the left (FIG. 8A) shows a mouse following treatment with ferric chloride ($FeCl_3$) for thrombus formation and following injection with a saline solution. The image to the right (FIG. 8B) shows a mouse following treatment with ferric chloride ($FeCl_3$) to induce a thrombus and following injection of the Tog25t-Control2-AF680 aptamer.

FIG. 9 shows near-infrared fluorescence images showing Tog25t-AF680 binding to a jugular vein thrombus in vivo in a mouse and then the reversal of the Tog25t-AF680 binding by treatment with the antidote AO4. The image to the left (FIG. 9A) shows a mouse before treatment with ferric chloride ($FeCl_3$) to induce a thrombus and before injection of the Tog25t-AF680 aptamer. The image in the middle (FIG. 9B) shows localization of fluorescence close to the site of injury (thrombus) following treatment with ferric chloride ($FeCl_3$) and following injection of the Tog25t-AF680 aptamer. The image to the right (FIG. 9C) shows the reversal of the Tog25t-AF680 fluorescence close to the site of the thrombus injury following injection of the antidote oligonucleotide AO4.

Figures 10, 10A, 10B:
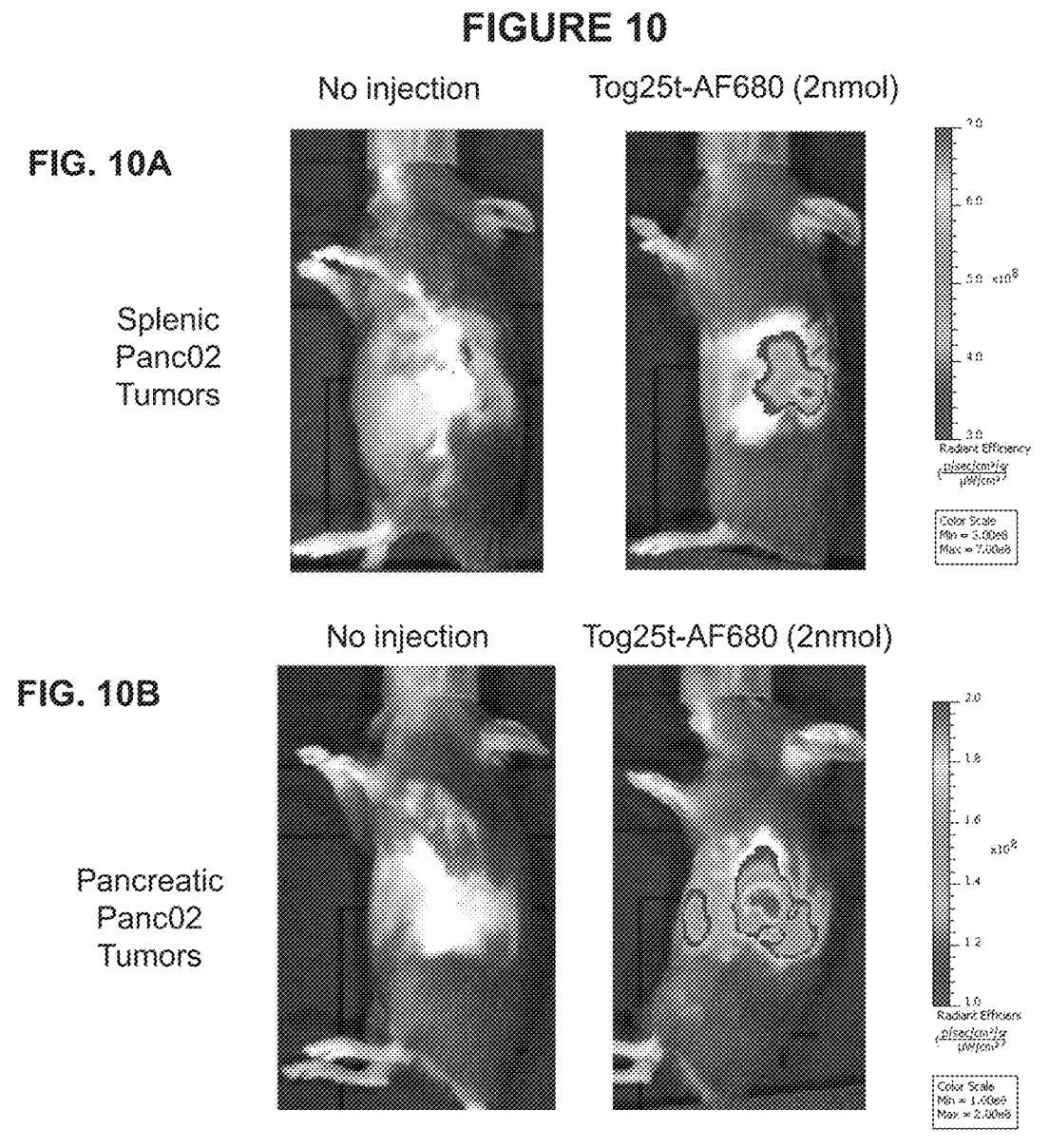

FIG. 10 shows near-infrared fluorescence images showing Tog25t-AF680 binding and localization to activated thrombin in Panc02 splenic and pancreatic tumors in vivo in mice. The images in FIG. 10A show the localization of fluorescence signal to activated thrombin in a mouse bearing a splenic Panc02 tumor and injected with the Tog25t-AF680 aptamer (right), compared to a non-injected splenic Panc02 tumor-bearing mouse (left). The images in FIG. 10B show the localization of fluorescence signal to activated thrombin in a mouse bearing a pancreatic Panc02 tumor and injected with the Tog25t-AF680 aptamer (right), compared to a non-injected pancreatic Panc02 tumor-bearing mouse (left).

DETAILED DESCRIPTION

The present disclosure is based, in part, on the finding that aptamer-based imaging agents are useful tools for detecting a thrombus or thrombin. Disclosed herein are compositions of imaging agents and antidotes as well as methods for imaging a thrombus and thrombin and for generating subtraction images using aptamer-based imaging agents and antidotes. These compositions and methods may be useful in several clinical applications including, without limitation, general thrombi imaging (in vitro, in vivo, or ex vivo), stroke, cerebrovascular thrombi, deep vein thrombosis (DVT), pulmonary embolism (PE), atrial fibrillation, coronary artery thrombus, intra-cardiac thrombi, post-surgical thrombi, cancer-induced thrombosis, cancer-induced thrombin activation, infection-induced thrombin activation, and disseminated intravascular coagulation (DIC).

Imaging agents are provided herein. The imaging agents may include (a) an aptamer linked to (b) a reporter moiety. The aptamer binds thrombin with a Kd<1 µM, 500 nM, 250 nM, 100 nM, 50 nM, 10 nM, 1 nM, 0.5 nM or 0.1 nM. The aptamer may include a nucleotide sequence having at least 50%, 60%, 70%, 80%, 90%, or 95% sequence identity to GGGAACAAAGCUGAAGUACUUACCC (Tog25t; SEQ ID NO: 1). Alternatively, the aptamer may include a nucleotide sequence including from 5' to 3' a first stem forming region comprising at least three nucleotides, a first loop region comprising the nucleotide sequence AACA (adenine-adenine-cytosine-adenine), a second stem forming region comprising at least three nucleotides, a second loop region comprising the nucleotide sequence C U/A GXAG U/A A, a third stem forming region comprising at least three nucleotides capable of forming a stem with the second stem forming region, a third loop region comprising at least one nucleotide and up to 5 nucleotides, suitably a single adenine (A) nucleotide, and a fourth stem forming region comprising at least three nucleotides capable of forming a stem with the first stem forming region. The single letter codes stand for the traditional bases found in DNA or RNA and the X indicates that any of the four bases may be present at that position.

As used herein a "loop region" indicates that the nucleotides in this region are not expected to base pair with any other nucleotides in the aptamer. As used herein "capable of forming a stem" and "stem forming region" indicate that the nucleotides in a particular region of the aptamer are paired with the nucleotides in a corresponding region such that they are reverse complements of each other and the bases in the nucleotides are expected to align in a base pairing relationship with each other to stabilize the three-dimensional structure of the aptamer. As is well known in the art, adenine forms hydrogen bonds with uracil or thymine and cytosine and guanine also form hydrogen bonds with each other in both DNA and RNA molecules. The bases align with their reverse complement either on separate nucleic acid strands or on the same nucleic acid strand.

Figures 1, 1A, 1B, 1C:
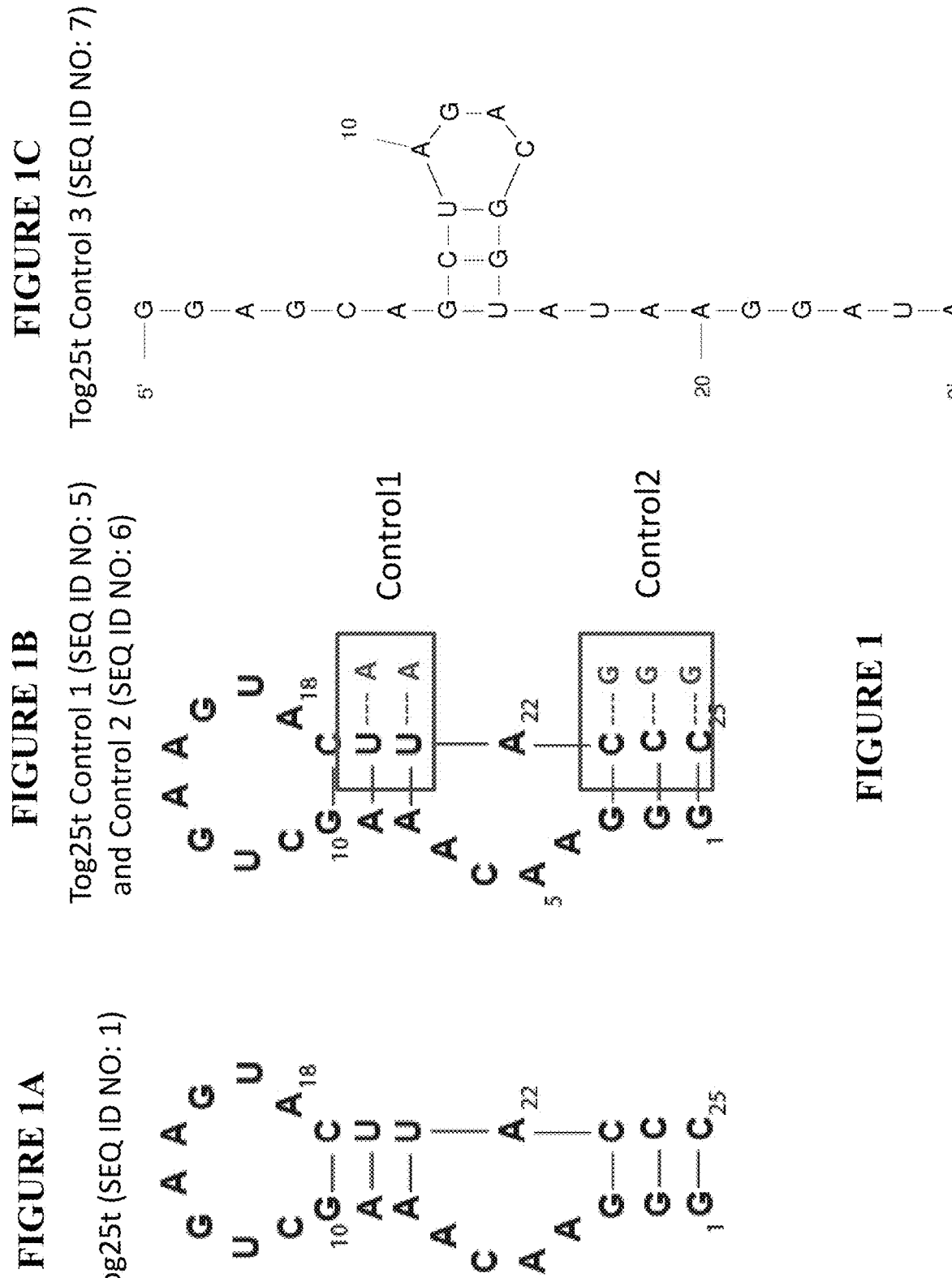
FIG. 1 shows the sequence and structure of the Tog25t aptamer (FIG. 1A; SEQ ID NO: 1) and Tog25t control aptamers (FIGS. 1B and 1C).
As shown in FIG. 1B, the Tog25t-Control1 aptamer has the same sequence as Tog25t except that the U bases at positions 20 and 21 are replaced with A bases (SEQ ID NO: 5). The Tog25t-Control2 aptamer has the same sequence as Tog25t except that the C bases at positions 23, 24, and 25 are replaced with G bases (SEQ ID NO: 6). The sequence and structure of Tog25t-Control3 is shown FIG. 1C (SEQ ID NO: 7).

As shown in FIG. 1A, one exemplary aptamer sequence is SEQ ID NO: 1 which is also referred to herein as Tog25t. Based on the structure presented in FIG. 1A, a person of ordinary skill in the art would readily recognize that several modifications could be made to the sequence while preserving the overall structure and presumably the function of the aptamer. For example, a person of ordinary skill in the art could simply switch the first three Gs and the last 3 Cs (e.g., CCCAACAAAGCUGAAGUACUUAGGG (SEQ ID NO: 8)) and still retain the stem structure of the aptamer. As an additional example the nucleotides in the second stem region could also be switched to those of SEQ ID NO: 9 (GGGAA-CAUUCCUGAAGUAGAAACCC) which is also expected to be a functional aptamer in the imaging agents provided herein. Finally, SEQ ID NO: 10 (CCCAACAUUCCUGA-AGUAGAAAGGG) shows an example aptamer in which both stem regions are transposed. A person of ordinary skill would also recognize that changes made to the aptamer that disturbed the stem loop structure (See, e.g., FIG. 1B or FIG. 1C, Tog25t-Controls 1-3) would result in an aptamer incapable of efficiently binding its target.

A person skilled in the art would also recognize that while the aptamers provided herein are RNA aptamers, the aptamers may be made of modified nucleotides or may include some deoxyribonucleotides, 2'-fluoro or 2'-O methyl groups in the RNA. In the examples, the RNA aptamers included 2'-Fluoro (2'-F) modified pyrimidines, 2'-hydroxyl (2'-OH) purines and a 3' inverted deoxythymidine (idT) residue for added stability from nuclease degradation. The aptamers may also be protected from RNase degradation by 3' or 5' modifications to the aptamer or by inclusion of modified bases such as locked nucleic acids (LNAs) or peptide nucleic acids (PNAs). Suitable aptamers are capable of binding to thrombin or other components of the thrombus, but are generally not very effective at dissolving or blocking formation of the thrombus. This function allows the aptamer to bind to and label the thrombus via the linkage to the reporter moiety.

As used herein, the term "aptamer" refers to single-stranded oligonucleotides that bind specifically to targets molecules with high affinity. Target molecules may include, without limitation, proteins, lipids, carbohydrates, or other types of molecules. Aptamers can be generated against target molecules, such as soluble coagulation proteins, by screening combinatorial oligonucleotide libraries for high affinity binding to the target (See, e.g., Ellington and Szostak, Nature 1990; 346:8 18-22 (1990), Tuerk and Gold, Science 249:505-1 0 (1990)). The aptamers disclosed herein may be synthesized using methods well-known in the art. For example, the disclosed aptamers may be synthesized using standard oligonucleotide synthesis technology employed by various commercial vendors including Integrated DNA Technologies, Inc. (IDT), Sigma-Aldrich, Life Technologies, or Bio-Synthesis, Inc.

A "reporter moiety" may include any suitable chemical or substance that may be detected as a signal or contrast using imaging techniques. Reporter moieties are well known in the art and have been summarized in, for example, James and Gambhir, *Physiol Rev* 92:897-965 (2012). In some embodiments, a reporter moiety may include a fluorophore moiety, an optical moiety, a magnetic moiety, a radiolabel moiety, an X-ray moiety, an ultrasound imaging moiety, a photoacoustic imaging moiety, a nanoparticle-based moiety, or a combination of two or more of the listed moieties. A reporter moiety may also include a therapeutic reporter such as a radionuclide used in radiotherapy or a porphyrin used in photodynamic therapy.

A "fluorophore moiety" may include any molecule capable of generating a fluorescent signal. Various fluorophore moieties are well-known in the art and/or commercially available. Exemplary fluorophore moieties include, without limitation, fluorescein, FITC; Alexa dyes such as Alexa Fluor 488 (AF488), Alexa Fluor 660 (AF660), Alexa Fluor 680 (AF680), Alexa Fluor 750 (AF750), and Alexa Fluor 790 (AF790) (Life Technologies); Cy dyes such as Cy2, Cy3, Cy3.5, Cy5, Cy5.5 and Cy7 (GE Healthcare); DyLight dyes DyLight 350, DyLight 488, DyLight 594, DyLight 650, DyLight 680, DyLight 755 (Life Technologies); IRDye dyes such as IRDye 800CW, IRDye 800RS, and IRDye 700DX (Li-Cor); VivoTag dyes such as VivoTag680, VivoTag-S680, and VivoTag-S750 (PerkinElmer). "Optical moieties" may include but are not limited to any agents that may be used to produce contrast or signal using optical imaging such as luminescence or acousto-optical moieties. "Magnetic moieties" may include a chelating agent for magnetic resonance agents. Chelators for magnetic resonance agents may be selected to form stable complexes with paramagnetic metal ions, such as Gd (III), Dy (III), Fe (III), and Mn (II). Other exemplary reporter moieties include "radiolabel moieties." Exemplary radiolabel moieties include, without limitation, $^{99m}$Tc, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{11}$C, $^{13}$N, $^{15}$O, and $^{18}$F. Exemplary reporter moieties may also include therapeutic radiopharmaceuticals including, without limitation, $^{186}$Re, $^{188}$Re, $^{153}$Sm, $^{67}$Cu, $^{105}$Rh, $^{111}$Ag, and $^{192}$Ir. "X-ray moieties" may include any agents that may be used to produce contrast or signal using X-ray imaging such as iodinated organic molecules or chelates of heavy metal ions. "Ultrasound imaging moieties" may include any agents that may be used to produce contrast or signal using ultrasound targeted microbubbles such as Levovist, Albunex, or Echovist. "Photoacoustic imaging moieties" may include photoacoustic imaging-compatible agents such as methylene blue, single-walled carbon nanotubes (SWNTs), and gold nanoparticles.

A reporter moiety may also be a nanoparticle-based moiety. A "nanoparticle-based moiety" may include a nanoparticle that is capable of generating a signal. For example, silicon containing nanoparticles may be used to produce fluorescence, luminescence, or other type of signal. Other exemplary nanoparticle-based moieties include, for example, nanospheres such as Kodak X-SIGHT 650, Kodak X-SIGHT 691, Kodak X-SIGHT 751 (Fisher Scientific); metal oxide nanoparticles; and quantum dots such as Evi-Tags (Evident Technologies) or Qdot probes (Life Technologies).

The aptamer and reporter moieties may be "linked" either covalently or noncovalently. Additionally, the aptamer and reporter moieties may be linked using a linker or spacer moiety. Useful linker or spacer moieties include peptides, amino acids, nucleic acids, as well as homofunctional linkers or heterofunctional linkers Particularly useful conjugation reagents that can facilitate formation of a covalent bond between an aptamer and reporter moiety may comprise an N-hydroxysuccinimide (NHS) ester and/or a maleimide or using click chemistry. In the Examples, 5'-thiol modified aptamers were reacted with maleimide modified dyes and 5'-amine modified aptamers were reacted with N-hydroxysuccinimide ester (NHS ester) modified dyes. The aptamer and reporter moiety may be linked at the 5' end or the 3' end of the aptamer or may be linked at any nucleotide internally if the nucleotide is first modified with the required functional group. In the examples, a C6 linker conjugated to either an amine or thiol moiety was added to the 5'-end to allow for subsequent reporter labeling.

The aptamer and the reporter moiety may be linked using a tag system. A "tag system" may include any group of agents capable of binding one another with a high affinity. Several tag systems are well-known in the art and include, without limitation, biotin/avidin, biotin/streptavidin, biotin/NeutrAvidin, or digoxigenin (DIG) systems. In some embodiments, said tag system comprises biotin/avidin or biotin/streptavidin. In such embodiments, the aptamer may be modified at either the S' or 3' end to include biotin while the reporter moiety may be modified to include streptavidin or avidin. Alternatively, the aptamer may be modified at either the 5' or 3' end to include streptavidin or avidin while the reporter moiety may be modified to include biotin.

Antidotes are also provided herein and include oligonucleotides capable of hybridizing via base complementarity to the aptamer resulting in a secondary structure change of the aptamer and thus preventing and even reversing the binding of an aptamer to its target. An antidote to the Tog25t aptamer of SEQ ID NO: 1 presented herein may include a nucleotide sequence having at least 50%, 60%, 70%, 80%, 90% or 95% sequence identity to one of the following sequences: GGGUAAGUACUUCAG (SEQ ID NO: 2), UUCAGCUUUGUUCCC (SEQ ID NO: 3) or UAAGUACUUCAGCUUU (SEQ ID NO: 4). Alternatively, an antidote may include a nucleotide sequence having 50%, 60%, 70%, 80%, 90%, 95%, or 100% sequence identity to a sequence complementary to and/or capable of hybridizing to at least 5, 6, 7, 8, 9, 10, 11, 12, 13, 14, 15, 16, 17, 18, 19, or 20 nucleotides present in the aptamers disclosed herein. The antidotes of SEQ ID NOs: 2-4 are shown as RNA antidotes, but the antidotes may suitably be DNA antidotes as used in the Examples and shown in FIG. 5. Those skilled in the art will appreciate that the sequences would be altered to include thymines in place of the uracils in the antidotes sequences of SEQ ID NO: 2-4 when in a DNA form. In the in vivo assays shown in the Examples the antidotes used were all 2'-O methyl RNA antidotes. Other modified nucleic acids could also be used in the antidotes as described above for the aptamers such as 2'-fluor modified nucleic acids, LNAs or PNAs.

In some embodiments, antidotes may further include a quencher capable of quenching a signal from a reporter moiety. As used herein, a "quencher" refers to any substance capable of absorbing energy from a reporter moiety or disrupting the function of the reporter moiety. Exemplary quenchers include, without limitation, Dabcyl, BHQ1, BHQ2, BHQ3, BBQ-650, QSY 7, QSY 9, and QSY 21. The quenchers may be linked to the antidotes. Means of linking and types of linkers that may be used to link the antidote and the quencher are similar to the linkers used in the imaging agents described above.

Methods for imaging a thrombus are also provided. The methods may include contacting a thrombus or thrombin (such as in cancer-activated thrombin imaging studies) with an imaging agent. The "contacting" may occur directly or indirectly in vitro, in vivo, or ex vivo. Contacting includes administration to a cell, tissue, or mammal and includes humans. Contacting a thrombus or thrombin includes adding the imaging agent to a cell culture or tissue culture containing a thrombus. The agent may also be more directly delivered or administered by any means available to those skilled in the art including the methods of administration described below. A thrombus may be formed in vitro using methods and assays known in the art including, without limitation, the aPTT Coagulation assay or the in vitro clot assay used in the Examples.

The methods may also include administering an imaging agent to a subject and generating an image of at least a portion of the subject using an imaging modality, wherein the imaging agent is capable of specifically labeling the thrombus in the image by binding of the aptamer to the thrombus. In further embodiments, the aptamer used in the imaging agent is capable of binding thrombin with a Kd<1 μM, 500 nM, 250 nM, 100 nM, 50 nM, 10 nM, 1 nM, 0.5 nM or 0.1 nM. In some embodiments, the method may further include administering any of the antidotes (or combinations thereof) disclosed herein to reverse or block the labeling of the thrombus by the imaging agent.

As used herein, "labeling" refers to generating a detectable signal within an image. Labeling is believed to be effected by binding of the aptamer to thrombin in the thrombus or activated thrombin and the reporter moiety linked to the aptamer can be used to generate a detectable signal to label the thrombus.

As used herein, an "imaging modality" may include any technology capable of generating an image of a subject (or a portion of a subject). The imaging modality may include any imaging technology including, without limitation, positron-emission tomography (PET), single photon emission computed tomography (SPECT), magnetic resonance imaging (MRI), optical imaging (OI), ultrasound, photoacoustic imaging (PAI), computed tomography (CT), or any combination of these imaging modalities. In some embodiments, the imaging modality may include near-infrared fluorescence (NIRF) imaging. Optical imaging may be completed using a standard confocal or fluorescent microscope.

As used herein, the term "subject" refers to both human and non-human animals. The term "non-human animals" of the disclosure includes all vertebrates, e.g., mammals and non-mammals, such as non-human primates, sheep, dog, cat, horse, cow, mice, chickens, amphibians, reptiles, and the like. In some embodiments, the subject is a human patient.

The methods of the present disclosure may include administering to a subject imaging agents and/or antidotes disclosed herein. Such "administering" can be local administration or systemic administration. Imaging agents and antidotes may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or transmucosal absorption. Thus the imaging agents and antidotes may be formulated as an ingestible, injectable, topical or suppository formulation or a part of an implant. The imaging agents and antidotes may also be delivered within a liposomal or time-release vehicle. Administration of the imaging agents or antidotes disclosed herein will be in an effective amount, which is an amount effective to image a suspected abnormality in a subject.

It will also be appreciated that the specific dosage of imaging agent and/or antidote administered in any given case will be adjusted in accordance with the composition or compositions being administered, the suspected abnormality to be imaged or treated, the condition of the subject, and other relevant medical factors that may modify the activity of the imaging agents and/or antidotes or the response of the subject, as is well known by those skilled in the art. For example, the specific dose for a particular subject depends on age, body weight, general state of health, diet, the timing and mode of administration, the rate of excretion, medicaments used in combination as well as other factors. Dosages for a given patient can be determined using conventional considerations, e.g., by customary comparison of the differential activities of the imaging agents and/or antidotes described herein and of a known agent, such as by means of an appropriate conventional pharmacological protocol.

The maximal dosage for a subject is the highest dosage that does not cause undesirable or intolerable side effects. The number of variables in regard to an individual imaging and/or treatment regimen is large, and a considerable range of doses is expected. The route of administration will also impact the dosage requirements.

The effective dosage amounts described herein refer to total amounts administered, that is, if more than one composition is administered, the effective dosage amounts correspond to the total amount administered. The imaging agents and/or antidotes can be administered as a single dose or as divided doses. For example, the imaging agents or antidotes may be administered two or more times separated by 30 minutes, 1 hour, 2 hours, 4 hours, 6 hours, 8 hours, 12 hours, a day, two days, three days or more.

The imaging agents and/or antidotes described herein may be administered one time or more than one time to the subject to effectively image a suspected abnormality in a subject. Suitable dosage ranges are of the order of several hundred micrograms effective ingredient with a range from about 0.001 to 10 mg/kg/day, preferably in the range from about 0.1 to 1 mg/kg/day. Precise amounts of effective imaging agent and/or antidote required to be administered depend on the judgment of the practitioner and may be peculiar to each subject. The imaging agents and antidotes may also be prepared for administration as pharmaceutical preparations and may include a pharmaceutically acceptable carrier or excipient. Examples of pharmaceutically acceptable carriers suitable for use include, but are not limited to, water, buffered solutions, glucose solutions, oil-based or bacterial culture fluids. Additional components of the compositions may suitably include, for example, excipients such as stabilizers, preservatives, diluents, emulsifiers and lubricants. Examples of pharmaceutically acceptable diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer).

Methods for generating a subtraction image are also provided. The methods may include administering an imaging agent to the subject, generating a first image of a portion of the subject, administering an antidote to the subject, generating a second image of the same portion of the subject, and subtracting the second image from said first image to generate said subtraction image. In an alternative embodiment, the methods may include contacting a thrombus or thrombin with the imaging agent, generating a first image of the thrombus or thrombin, contacting the thrombus or thrombin with an antidote, generating a second image of the thrombus or thrombin and subtracting the second image from said first image to generate said subtraction image. The subtraction image demonstrates the specificity of binding of the imaging agent to the thrombus or thrombin and represents an internal control for the specificity of the initial image. In subjects with cancer, prothrombin is cleaved to thrombin to create much higher than normal concentrations of thrombin. Cancer-induced thrombin activation can thus be monitored and studied using the methods described herein.

As used herein, "subtracting" two images refers to the process whereby the digital numeric value of one pixel or whole image is subtracted from another image. Methods for performing image subtraction are known within the art.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLE

Thrombin-Targeting Aptamer for Molecular Thrombi Imaging
Methods
Aptamer and Antidote Synthesis and Labelling We used four aptamers for our thrombi imaging studies: Tog25t, and three control aptamer sequences: Tog25t-Control1, Tog25t-Control2 and Tog25t-Control3 (FIG. 1, Table 1). Dye labeled versions of Tog25t, Tog25t-Control1, Tog25t-Control2, and Tog25t-Control3 were chemically synthesized by Bio-Synthesis, Inc. or an Oligonucleotide Synthesis core facility at Duke University. All RNA aptamers were synthesized using 2'-Fluoro (2'-F) modified pyrimidines, 2'-hydroxyl (2'-OH) purines and a 3' inverted deoxythymidine (idT) residue for added stability from nuclease degradation. A C6 linker conjugated to either an amine or thiol moiety was added to the 5'-end to allow for subsequent dye labeling.

TABLE 1

| Name | Sequence (5' to 3') | SEQ ID NO: |
|---|---|---|
| Tog25t | GGGAACAAAGCUGAAGUACUUACCC | SEQ ID NO: 1 |
| Tog25t-Control1 | GGGAACAAAGCUGAAGUACAAACCC | SEQ ID NO: 5 |

TABLE 1-continued

| Name | Sequence (5' to 3') | SEQ ID NO: |
|---|---|---|
| Tog25t-Control2 | GGGAACAAAGCUGAAGUACUUAGGG | SEQ ID NO: 6 |
| Tog25t-Control3 | GGAGCAGCUAGACGGUAUAAGGAUA | SEQ ID NO: 7 |

For the dye labeling reaction, aptamers were conjugated to Alexa Fluor 680 (AF680) or Cy5.5 dyes using one of two methods. 5'-thiol modified aptamers were reacted with maleimide modified dyes and 5'-amine modified aptamers were reacted with N-hydroxysuccinimide ester (NHS ester) modified dyes.

Antidote sequences were synthesized by Integrated DNA Technologies, Inc (IDT) and contained all deoxynucleotide residues for use in the aPTT assays (See Table 4 for the corresponding RNA sequences). The lead antidote sequence (AO4) was also synthesized by Bio-Synthesis, Inc and the sequence was comprised of 2'-O methyl (2'-O-Me) modified RNA residues at each position to confer nuclease stability for the in vivo assays aPTT Coagulation Assay aPTT assays were performed using a model ST4 coagulometer. 50 μL of normal platelet poor plasma (PPP) purchased from George King Biomedical was incubated with 1 μM aptamer or buffer for 5 minutes at 37° C. 50 μL of TriniCLOT aPTT S activator reagent (micronized silica) was added to the plasma/aptamer mix and incubated for 5 minutes at 37° C. 50 μL of 0.02 M calcium chloride (CaCl$_2$)) was then added to the mix to initiate clot formation and the time for clot formation was recorded. For antidote reversal studies, a 2-fold molar excess of antidote was added to the plasma/aptamer/activator mix for 5 minutes at 37° C. prior to CaCl$_2$) addition.
In Vitro Clot Assays Human plasma clots were formed from 180 μL platelet poor plasma (PPP) in 96 well plates with 10 μL 0.4 M CaCl$_2$) and 10 μL phosphate-buffered saline (PBS). 50 pmol of a non-specific binder (such as yeast tRNA) was added to the newly formed clots for 30 minutes prior to addition of 10 pmol of RNA (labeled Tog25t, Control2 or Control3). Aptamers were incubated with the clots for 30 minutes at 37° C., and then the clots were washed with PBS prior to fluorescence imaging. For antidote reversal studies, clots that were treated with aptamers prior to imaging were then incubated with a 5-fold excess of AO4 for 10 minutes at 37° C. Clots were subsequently washed and then imaged again.
Venous Thrombosis Model and FMT Imaging In vivo thrombus imaging studies were performed using C57BL/6J mice. First, mice were anesthetized using isoflurane at an induction dose of 3% and a maintenance dose of 1.5%. All hair on the ventral and dorsal neck and chest was then removed using a depilatory cream to prepare for imaging. Pre-injection, pre-surgery images were obtained via fluorescence molecular tomography (FMT) using a Perkin Elmer VisEn FMT2500LX. After pre-injection imaging, mice were injected via the tail vein with either saline control or 2 nmoles of aptamer-NIR dye conjugates. Two different aptamer-Alexa Fluor 680 (AF680) NIR dye conjugates were injected for imaging: thrombin-binding Tog25t-AF680 or the non-binding point mutant control, Tog25t-Control2-AF680.

After aptamer injection, mice were anesthetized via intraperitoneal (ip) injection of both 3 mg/kg acepromazine and 100 mg/kg ketamine with 10 mg/kg xylazine from a 10:1 mixture of ketamine and xylazine in sterile saline. Mouse body temperature was maintained at approximately 37° C. using a Physitemp TCAT-2DF. Mice were subsequently monitored to ensure a surgical plane of anesthesia was maintained and were redosed with 30 mg/kg of ketamine and 3 mg/kg of xylazine as needed. After ensuring a surgical plane of anesthesia, an incision of the skin was made, and the fascia bluntly dissected to expose the jugular vein. After isolation of the jugular vein, a 5% FeCl₃ patch (2 mm×4 mm) was placed on the ventral aspect of the exposed vein and left in place for 1 minute. Upon removal of the patch, the vein was lightly rinsed with 0.9% saline. The skin incision was then sutured closed in a simple continuous pattern. After surgery, at a time point ~50 minutes post-aptamer injection, post-injection NIR fluorescent images were obtained using a Perkin Elmer VisEn FMT2500LX.

After this NIR imaging, mice being treated with the antidote were injected via tail vein with 10 nmoles of antidote AO4. Immediately after antidote injection (within 4 minutes), post-antidote injection NIR fluorescent images were obtained using a Perkin Elmer VisEn FMT2500LX.

Venous Cancer-Induced Thrombin Activation Model and IVIS Lumina Imaging

In vivo tumor imaging studies were performed using C57BL/6J mice. First, tumors were implanted by anesthetizing mice at an induction dose of 3-5% isoflurane. Immediately after induction, mice received buprenorphine (0.05 to 0.10 mg/kg) subcutaneously in a volume of 50-200 μL with a saline vehicle. While maintaining a maintenance isoflurane dose of 1-3%, hair was removed from the ventral abdomen by either shaving or use of a depilatory cream. The surgical site on the abdomen was then prepped with a povidone/iodine (or chlorhexidine) skin scrub followed by an alcohol rinse with sterile gauze, for a total of three times. The mice were subsequently placed in right lateral recumbency and the surgical site draped with either plastic wrap or sterile drapes before making a 1.5 cm longitudinal incision in the skin 1 cm left-lateral of midline, slightly medial to the spleen. An additional 1.5 cm incision was made in the abdominal musculature, mirroring the overlying superficial incision before retracting the spleen and pancreas from the abdominal cavity using a sterile cotton tipped applicator. 25 μL of a Panc02 cell suspension (1×10⁵ cells resuspended 1:1 in RPMI:Matrigel, for a total volume of 50 μL) was then slowly injected into the spleen or the head of the pancreas over 30-60 seconds. After injection, the spleen and the pancreas were gently returned to the abdominal cavity and 0.25% bupivacaine (diluted to 0.125% with sterile saline) dripped between the abdominal and cutaneous layers at no more than a maximum dose of 2 mg/kg (approximately 15-40 L). The abdominal musculature was sutured closed with non-absorbable suture and buprenorphine (0.05 to 0.10 mg/kg) given subcutaneously in a volume of 50-200 μL with a saline vehicle every 12 hours as needed for pain. Once the surgical wound healed, approximately 7-10 days later, anesthesia was induced with 3 to 5% isoflurane. Sutures were then quickly removed.

Six weeks later, after the mice had formed visible tumors, mice were injected via the tail vein with 2 nmoles of aptamer-Alexa Fluor 680 (AF680) NIR dye conjugate. 30 minutes after aptamer injection, both aptamer-injected and non-injected control mice were anesthetized with 3% isoflurane and imaged for NIR fluorescence using an IVIS Lumina XR.

Results

Tog25t is a thrombin-targeting aptamer. See, e.g., Long, S. B., et al. *RNA*. 14, 2504-2512 (2008). Tog25t binds to human thrombin (Table 2) and produces a modest extension in aPTT clotting time at relatively high concentrations of

Figure 2:
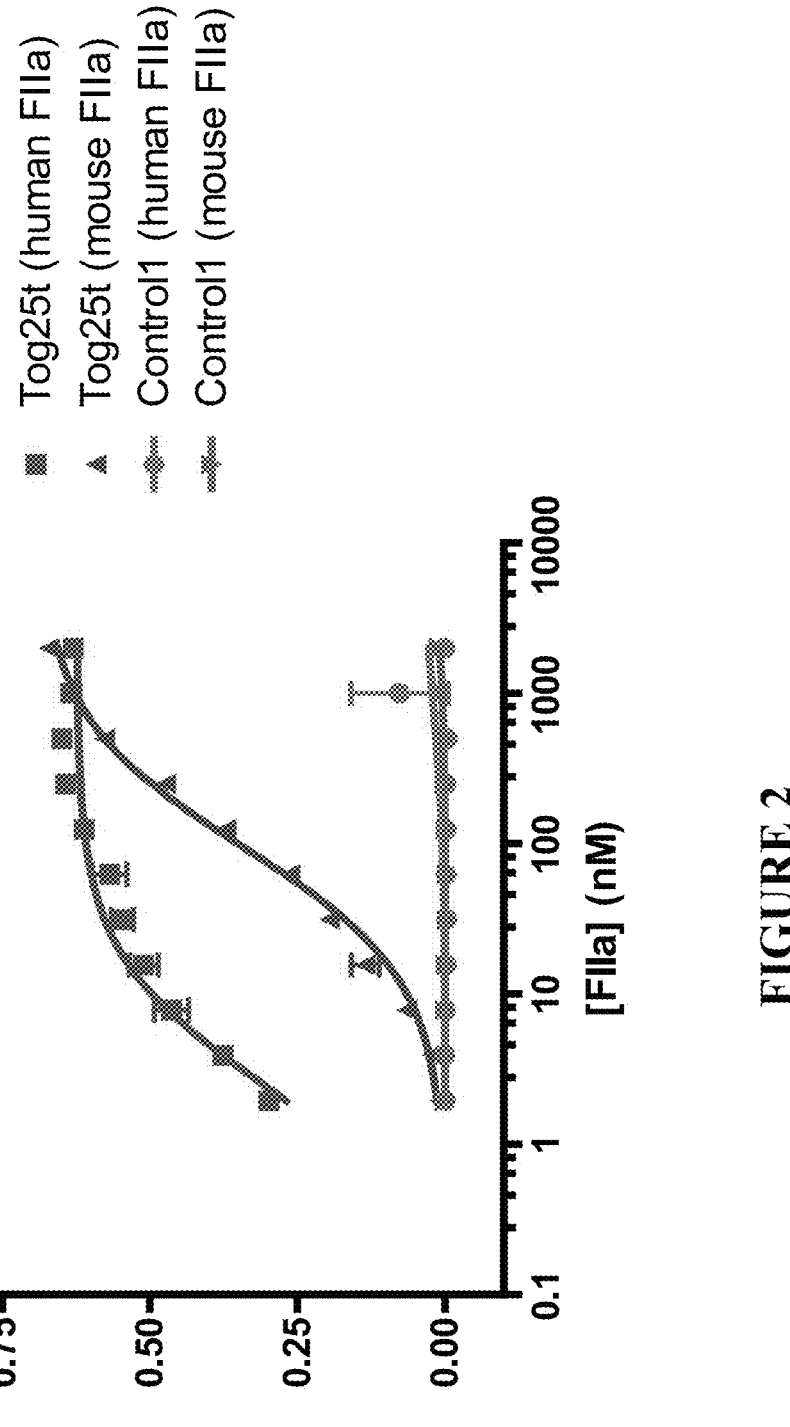
FIG. 2 shows binding curves for Tog25t and Tog25t-Control1 binding to both human and mouse Factor IIa (FIIa). Tog25t binds to mouse and human thrombin in plasma.

14 approximately 1 μM (Table 3). The cross reactivity of Tog25t with mouse thrombin was tested in both nitrocellulose filter-binding assays using purified mouse thrombin (FIG. 2) and in in vitro coagulation assays using mouse plasma (Table 3). Tog25t binds to mouse thrombin with a substantially lower affinity (Table 2) and approximately doubles the aPTT clotting time of plasma from female C57BL/6 mice at relatively high concentrations of approximately 1 μM (Table 3).

TABLE 2

| | Kd (nM) |
|---|---|
| Human FIIa | 2.57 |
| Mouse FIIa | 95.8 |

TABLE 3

| | Pooled human plasma (s) | Pooled female C57BL/6 mouse plasma (s) |
|---|---|---|
| Buffer | 28.5 | 26.3 |
| Tog25t | 51.3 | 52.5 |

Figures 3, 3A, 3B:
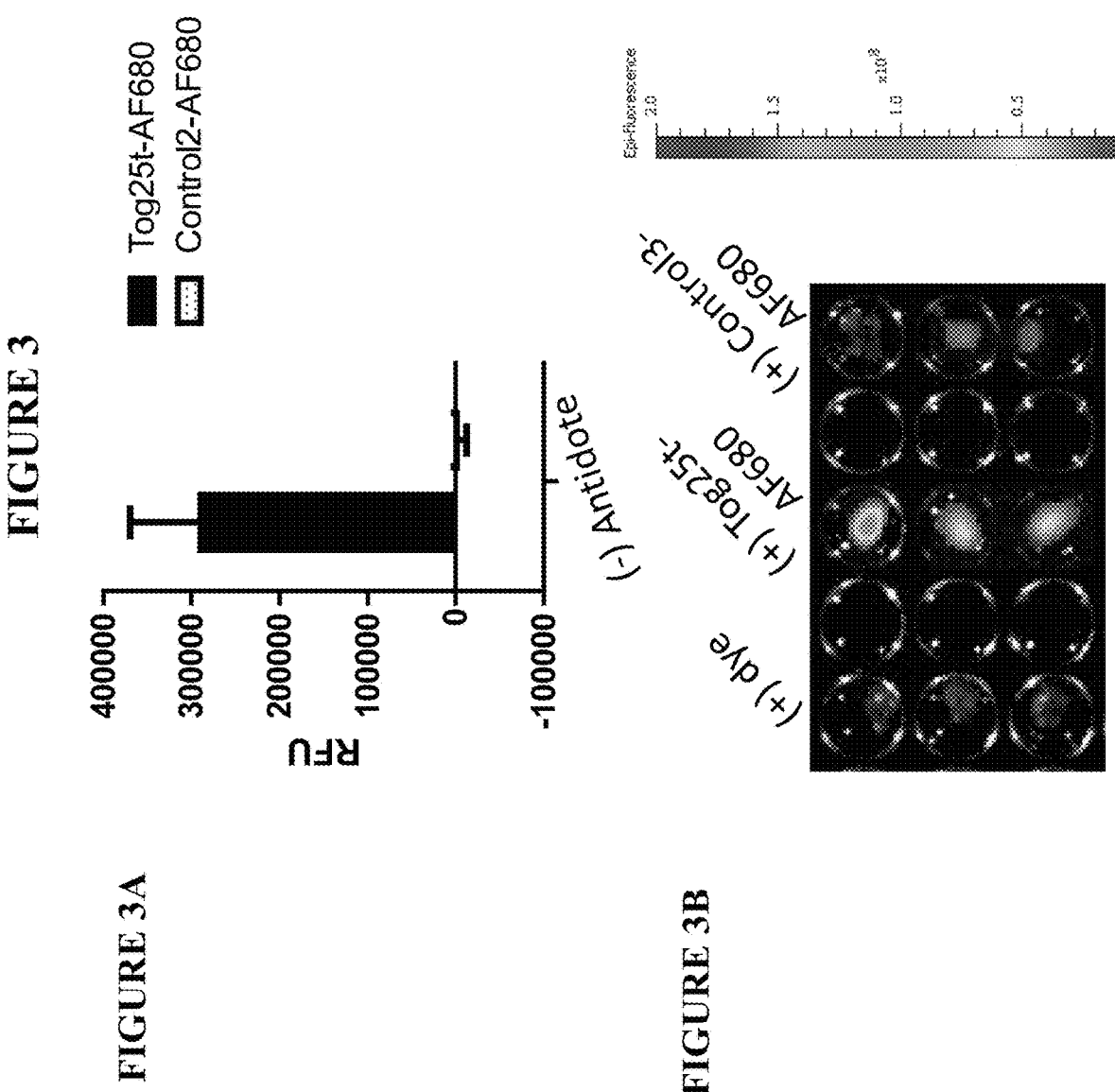
FIG. 3 shows data from in vitro clot assays.
FIG. 3A shows a bar graph summarizing fluorescence readings of Tog25t-AF680 and Tog25t-Control2-AF680 binding to in vitro plasma clots.
FIG. 3B shows images of Tog25t-AF680 binding to in vitro plasma clots in comparison to dye only or Tog25t-Control3-AF680.

To determine whether Tog25t could bind to clots, we generated human plasma clots in vitro, and treated them with Tog25t conjugated to Alexa Fluor 680 ("AF680," a near-infrared dye). We observed a significant enhancement in fluorescence in the presence of Tog25t-AF680 in comparison to Tog25t-Control3-AF680 or dye only (FIG. 3B).

Figure 5:
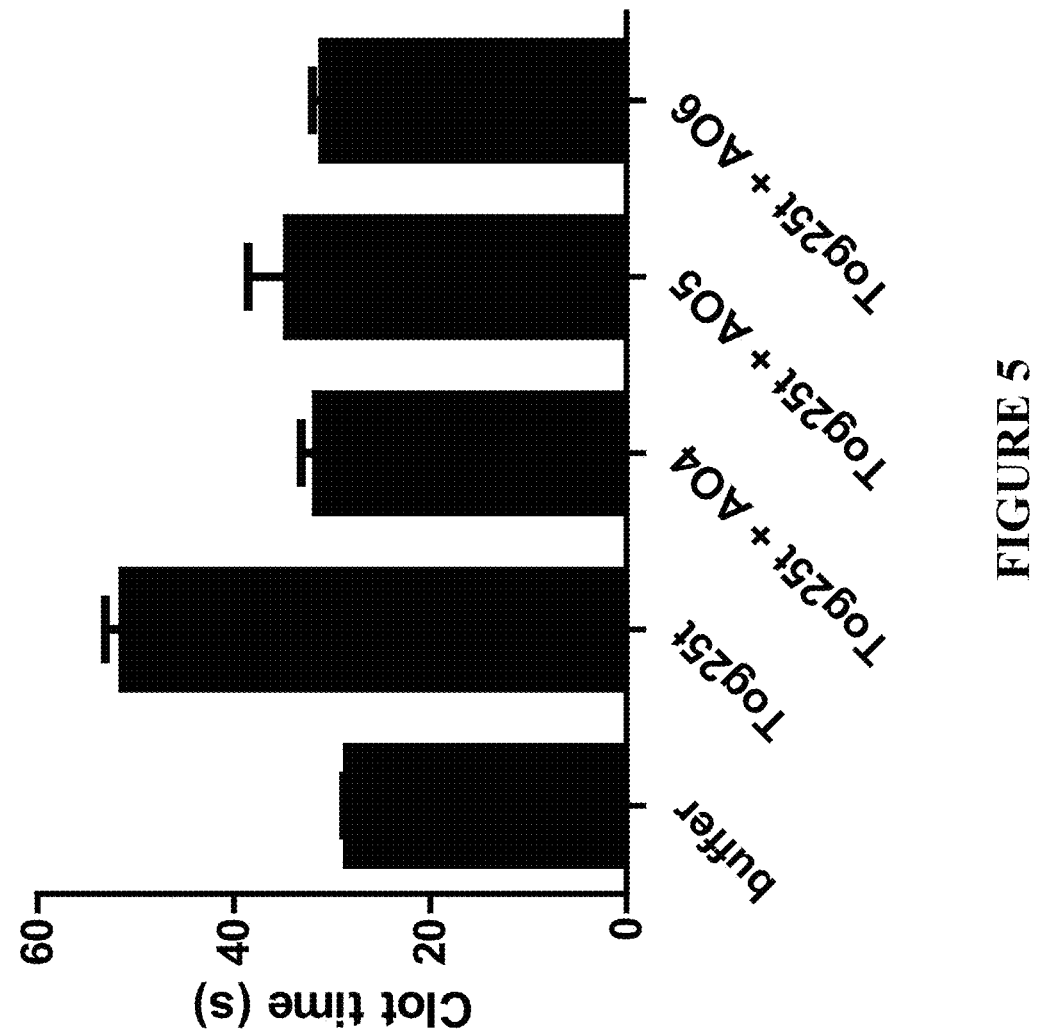
FIG. 5 shows a bar graph summarizing the clot times of human plasma in an aPTT coagulation assay for buffer, Tog25t, and Tog25t activity reversed with antidotes AO4-6 (the antidote molecules used in this assay were DNA antidotes).
Figure 6:
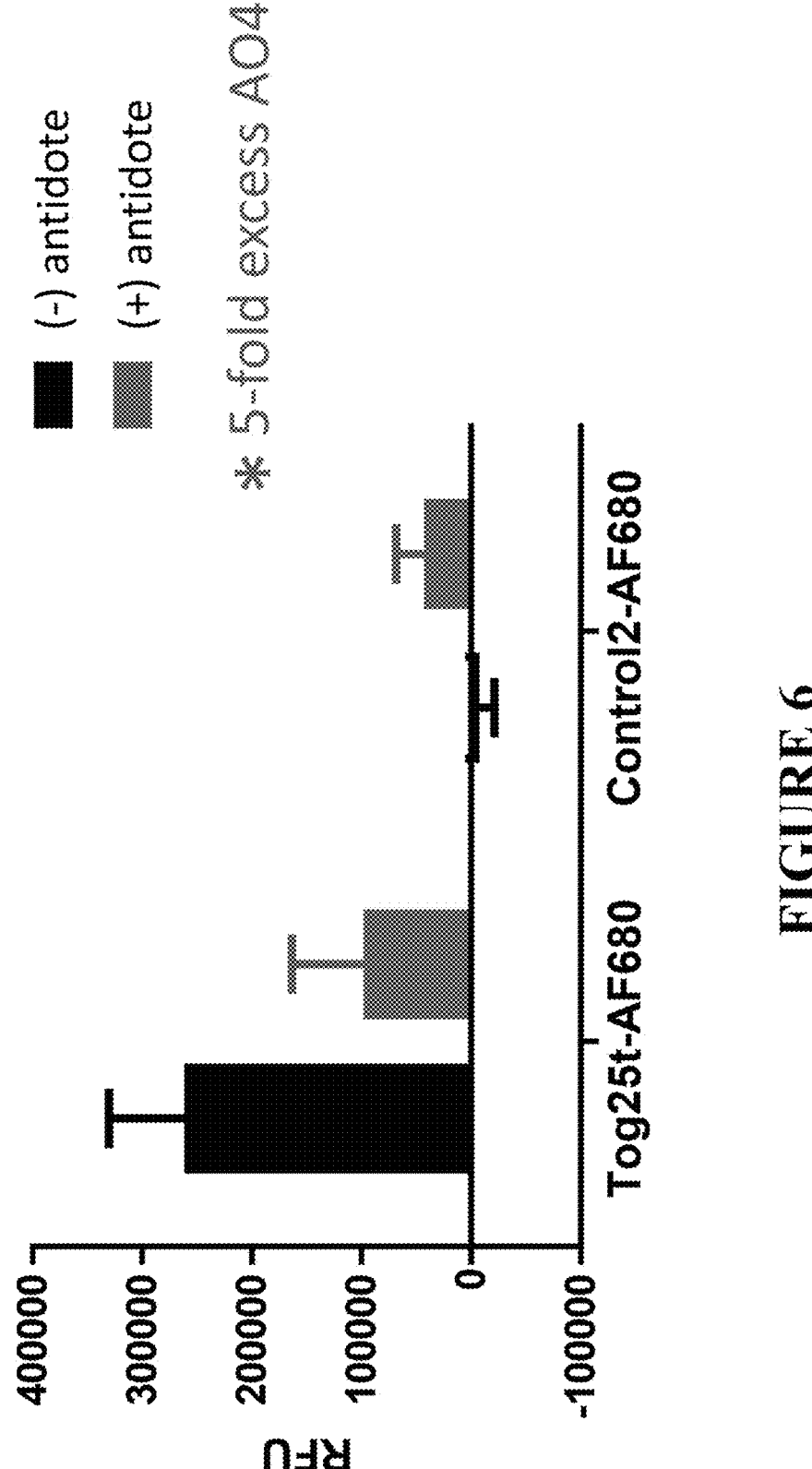
FIG. 6 shows a bar graph summarizing fluorescence readings of Tog25t-AF680 and Tog25t-Control2-AF680 binding to in vitro plasma clots before and after addition of antidote AO4 showing reversal of Tog25t binding to the plasma clot.

To reverse the binding of Tog25t to thrombin, we designed several antidote sequences against Tog25t (AO4-6, FIG. 4, Table 4) and tested the ability of the each sequence to reverse the anticoagulant activity of Tog25t in an aPTT clotting assay. Each of the sequences tested was able to bind to and reverse Tog25t's function (FIG. 5). AO4 was chosen as the lead antidote for further studies. Additional plasma clot assays were performed in order to determine whether AO4 was able to remove clot-bound Tog25t-AF680. A 5-fold molar excess of antidote oligonucleotide (AO4) was added to the Tog25t-bound clots after initial fluorescence readings were taken. AO4 was able to specifically remove clot-bound Tog25t-AF680 in comparison to Tog25t-Control2-AF680 as evidenced by the decrease in fluorescence signal after treatment (FIG. 6).

TABLE 4

| Name | Sequence (5' to 3') | SEQ ID NO: |
|---|---|---|
| AO4 | GGGUAAGUACUUCAG | SEQ ID NO: 2 |
| AO5 | UUCAGCUUUGUUCCC | SEQ ID NO: 3 |
| AO6 | UAAGUACUUCAGCUUU | SEQ ID NO: 4 |

We have also performed preliminary in vivo studies by inducing a sub-occlusive thrombus via ferric chloride injury to the mouse jugular vein. Tog25t-AF680 was injected prior to clot formation and the mice were imaged using a Fluorescence Molecular Tomography (FMT) imager before and after surgery. Our results suggest that Tog25t-AF680 localizes at the site of injury (FIG. 7B) when compared to the image of the same mouse prior to ferric chloride treatment and prior to injection of the aptamer (FIG. 7A) or to a normal mouse that had the injury but no Tog25t-AF680 aptamer injected (FIG. 8A). Injection of Tog25t-Control2-AF680 after ferric chloride treatment also failed to localize significant amounts of the AF680 dye to the site of injury suggesting the localization of Tog25t to the site of injury was specific and required the Tog25t sequence and structure (FIG. 8B). Our results also suggest that the Tog25t-AF680 localization at the site of injury is reversed by injection of an antidote. After Tog25t-AF680 localizes at the site of injury (FIG. 9B) when compared to the image of the same mouse prior to ferric chloride treatment and prior to injection of the aptamer (FIG. 9A), the Tog25t-AF680 localization can be reversed by injection of the antidote AO4 (FIG. 9C).

We have also performed preliminary in vivo studies in mice bearing splenic or pancreatic Pan02 tumors, which have high levels of thrombin activation. Mice bearing either splenic or pancreatic tumors were injected with Tog25t-AF680 and imaged using an IVIS Lumina XR imager. Our results suggest that Tog25t-AF680 localizes to activated thrombin in splenic Panc02 tumors when compared to a non-injected control mouse (FIG. 10A). Our results also suggest that the Tog25t-AF680 localizes to activated thrombin in pancreatic Panc02 tumors when compared to a non-injected control mouse (FIG. 10B).

Our results suggest that thrombin is a suitable target for imaging newly formed clots and that a RNA aptamer conjugate binds to clot-bound thrombin with high specificity. Additionally, our results suggest that thrombin is a suitable target for imaging diseases with thrombin-activation such as cancer and that a RNA aptamer conjugate binds to thrombin with high specificity. This thrombin-targeting near-infrared agent has the potential to be used as a diagnostic tool for arterial and venous thrombosis and for thrombogenic diseases such as cancer and such tools may further advance our understanding of the role of thrombin in vivo.

---

We claim:

1. An imaging agent comprising (a) an aptamer linked to (b) a reporter moiety, wherein said aptamer is capable of binding thrombin with a Kd<500 nM, wherein the aptamer comprises a nucleotide sequence having at least 70% sequence identity to SEQ ID NO: 1 or comprises a nucleotide sequence including from 5' to 3' a first stem forming region comprising at least three nucleotides, a first loop region comprising the nucleotide sequence AACA, a second stem forming region comprising at least three nucleotides, a second loop region comprising the nucleotide sequence C U/A GXAG U/A A, a third stem forming region comprising at least three nucleotides capable of forming a stem with the second stem forming region, a third loop region comprising at least one nucleotide and up to 5 nucleotides, and a fourth stem forming region comprising at least three nucleotides capable of forming a stem with the first stem forming region, wherein A is adenine, C is cytosine, G is guanine, U is uracil and X is any base in the nucleotide sequences.

2. The imaging agent of claim 1, wherein said reporter moiety is selected from the group consisting of a fluorophore moiety, an optical moiety, a magnetic moiety, a radiolabel moiety, an X-ray moiety, an ultrasound imaging moiety, a photoacoustic imaging moiety, a nanoparticle-based moiety, and a combination of two or more of the recited moieties.

3. The imaging agent of claim 2, wherein said reporter moiety comprises a fluorophore moiety.

4. The imaging agent of claim 1, wherein said aptamer and said reporter moiety are linked by a covalent bond.

5. The imaging agent of claim 4, wherein said aptamer and said reporter moiety are linked at the 5' or 3' end of said aptamer.

6. The imaging agent of claim 1, wherein said aptamer and said reporter moiety are linked by a tag system.

7. The imaging agent of claim 1, wherein the aptamer and the reporter moiety are linked with a 5'-Thiol-modified C6 linker.

8. The imaging agent of claim 7, wherein the reporter moiety comprises a maleimide modified dye.

9. The imaging agent of claim 8, wherein the reporter moiety is Cy5.5.

10. The imaging agent of claim 1, wherein the aptamer and the reporter moiety are linked with a 5'-amine-modified C6 linker.

11. The imaging agent of claim 10, wherein the reporter moiety comprises a N-hydroxysuccinimide ester modified dye.

12. The imaging agent of claim 11, wherein the reporter moiety is Alexa Fluor 680.

13. The imaging agent of claim 6, wherein the tag system is selected from the group consisting of biotin/avidin, biotin/streptavidin, and biotin/deglycosylated avidin.

14. A method for imaging a thrombus or site of thrombin accumulation comprising administering the imaging agent of claim 1 and generating an image of at least a portion of the thrombus using an imaging modality, wherein the imaging agent labels said thrombus or site of thrombin accumulation in the image by binding of the aptamer to the thrombus.

15. The method of claim 14, further comprising administering an antidote to reverse or block the labeling of the thrombus or thrombin by the imaging agent, the antidote comprising a nucleotide sequence having at least 70% sequence identity to a nucleotide sequence selected from the group consisting of SEQ ID NO: 2, SEQ ID NO: 3 and SEQ ID NO: 4 and is complementary to at least 10 nucleotides of the aptamer.

16. A method for generating a subtraction image of a thrombus or thrombin accumulation in a subject comprising:

(a) administering the imaging agent of claim 1 wherein the aptamer binds to a thrombus or thrombin;

(b) generating a first image of a portion of the subject;

(c) administering an antidote that binds to the aptamer of the imaging agent in (a); wherein the antidote has at least 70% sequence identity to a nucleotide sequence selected from the group consisting of SEQ ID NO: 2, SEQ ID NO: 3 and SEQ ID NO: 4 and is complementary to at least 10 nucleotides of the aptamer;

(d) generating a second image of the portion of the subject; and (e) subtracting the second image of (d) from the first image of (b) to generate said subtracted image.

17. A method of diagnosing an arterial or venous thrombosis in a subject comprising:

(a) administering the imaging agent of claim 1 wherein the aptamer binds to a thrombus or thrombin;

(b) generating a first image of a portion of the subject;

(c) administering an antidote that binds to the aptamer of the imaging agent in (a); wherein the antidote has at least 70% sequence identity to a nucleotide sequence selected from the group consisting of SEQ ID NO: 2, SEQ ID NO: 3 and SEQ ID NO: 4 and is complementary to at least 10 nucleotides of the aptamer;

(d) generating a second image of the portion of the subject; and (e) subtracting the second image of (d) from the first image of (b) and using the subtracted image to determine if a thrombus is present and diagnosing the arterial or venous thrombosis in the subject if the thrombus is present.

\* \* \* \* \*

SEQUENCE LISTING

```
Sequence total quantity: 10
SEQ ID NO: 1               moltype = RNA   length = 25
FEATURE                    Location/Qualifiers
misc_feature               1..25
                           note = Synthetic oligonucleotide: Tog25t
source                     1..25
                           mol_type = other RNA
                           organism = synthetic construct
SEQUENCE: 1
gggaacaaag ctgaagtact taccc                                         25

SEQ ID NO: 2               moltype = RNA   length = 15
FEATURE                    Location/Qualifiers
misc_feature               1..15
                           note = Synthetic oligonucleotide: AO4
source                     1..15
                           mol_type = other RNA
                           organism = synthetic construct
SEQUENCE: 2
gggtaagtac ttcag                                                    15

SEQ ID NO: 3               moltype = RNA   length = 15
FEATURE                    Location/Qualifiers
misc_feature               1..15
                           note = Synthetic oligonucleotide: AO5
source                     1..15
                           mol_type = other RNA
                           organism = synthetic construct
SEQUENCE: 3
ttcagctttg ttccc                                                    15

SEQ ID NO: 4               moltype = RNA   length = 16
FEATURE                    Location/Qualifiers
misc_feature               1..16
                           note = Synthetic oligonucleotide: AO5
source                     1..16
                           mol_type = other RNA
                           organism = synthetic construct
SEQUENCE: 4
taagtacttc agcttt                                                   16

SEQ ID NO: 5               moltype = RNA   length = 25
FEATURE                    Location/Qualifiers
misc_feature               1..25
                           note = Synthetic oligonucleotide: Tog25t-Control1
source                     1..25
                           mol_type = other RNA
                           organism = synthetic construct
SEQUENCE: 5
gggaacaaag ctgaagtaca aaccc                                         25

SEQ ID NO: 6               moltype = RNA   length = 25
FEATURE                    Location/Qualifiers
misc_feature               1..25
                           note = Synthetic oligonucleotide: Tog25t-Control2
source                     1..25
```

-continued

```
                        mol_type = other RNA
                        organism = synthetic construct
SEQUENCE: 6
gggaacaaag ctgaagtact taggg                                              25

SEQ ID NO: 7            moltype = RNA   length = 25
FEATURE                 Location/Qualifiers
misc_feature            1..25
                        note = Synthetic oligonucleotide: Tog25t-Control3
source                  1..25
                        mol_type = other RNA
                        organism = synthetic construct
SEQUENCE: 7
ggagcagcta gacggtataa ggata                                              25

SEQ ID NO: 8            moltype = RNA   length = 25
FEATURE                 Location/Qualifiers
misc_feature            1..25
                        note = Synthetic oligonucleotide
source                  1..25
                        mol_type = other RNA
                        organism = synthetic construct
SEQUENCE: 8
cccaacaaag ctgaagtact taggg                                              25

SEQ ID NO: 9            moltype = RNA   length = 25
FEATURE                 Location/Qualifiers
misc_feature            1..25
                        note = Synthetic oligonucleotide
source                  1..25
                        mol_type = other RNA
                        organism = synthetic construct
SEQUENCE: 9
gggaacattc ctgaagtaga aaccc                                              25

SEQ ID NO: 10           moltype = RNA   length = 25
FEATURE                 Location/Qualifiers
misc_feature            1..25
                        note = Synthetic oligonucleotide
source                  1..25
                        mol_type = other RNA
                        organism = synthetic construct
SEQUENCE: 10
cccaacattc ctgaagtaga aaggg                                              25
```